(12) United States Patent
Forderer et al.

(10) Patent No.: US 9,101,426 B2
(45) Date of Patent: Aug. 11, 2015

(54) CABLE PLUG

(71) Applicant: Stryker Trauma AG, Selzach (CH)

(72) Inventors: Aaron Forderer, Biel / Bienne (CH);
Nicolas Hainard, Fontainemelon (CH);
Axel Bernhard Cremer, Lommiswil (CH)

(73) Assignee: Stryker Trauma SA (CH)

( * ) Notice: Subject to any disclaimer, the term of this patent is extended or adjusted under 35 U.S.C. 154(b) by 166 days.

(21) Appl. No.: 13/649,249

(22) Filed: Oct. 11, 2012

(65) Prior Publication Data

US 2014/0107710 A1 Apr. 17, 2014

(51) Int. Cl.
*A61B 17/82* (2006.01)
*A61B 17/84* (2006.01)
*A61B 17/88* (2006.01)
*A61B 17/80* (2006.01)

(52) U.S. Cl.
CPC .............. *A61B 17/82* (2013.01); *A61B 17/842* (2013.01); *A61B 17/8861* (2013.01); *A61B 17/80* (2013.01)

(58) Field of Classification Search
CPC ... A61B 17/82; A61B 17/8861; A61B 17/842
USPC ........... 606/300, 301, 305, 306, 74, 232, 246, 606/263
See application file for complete search history.

(56) References Cited

U.S. PATENT DOCUMENTS

| | | |
|---|---|---|
| 1,025,008 A | 4/1912 | Miner |
| 1,159,863 A | 4/1913 | Park |
| 2,226,393 A | 12/1940 | Seeger et al. |
| 3,534,731 A | 10/1970 | Muller |
| 3,547,114 A | 12/1970 | Haboush |
| 3,596,656 A | 8/1971 | Kaute |
| 3,997,138 A | 12/1976 | Crock et al. |
| 4,146,022 A | 3/1979 | Johnson et al. |

(Continued)

FOREIGN PATENT DOCUMENTS

| | | |
|---|---|---|
| DE | 202004015582 U1 | 12/2004 |
| EP | 0075225 A2 | 3/1983 |

(Continued)

OTHER PUBLICATIONS

Howmedica Osteonics, DALL-MILES Cable System, 2000.

(Continued)

*Primary Examiner* — Anu Ramana
(74) *Attorney, Agent, or Firm* — Lerner, David, Littenberg, Krumholz & Mentlik, LLP

(57) ABSTRACT

Disclosed herein are cable plugs for securing surgical cable to a bone plate. The cable plugs each have a cable retaining member and a fastening member. The cable retaining members each have a receiving portion adapted to receive a portion of the surgical cable therein. The cable retaining members are first coupled to the fastening members prior to securing the cable plug to the bone plate. The cable retaining member may rotate with respect to the fastening member about 270° along a longitudinal axis of the cable plug when the cable retaining member is coupled to the fastening member. When securing the surgical cable to the bone plate, the cable retaining member is rotated about the longitudinal axis of the cable plug until an axis of the receiving portion is parallel to an axis of the surgical cable. The surgical cable is then placed within the receiving portion, tightened, and crimped to secure the bone plate to the bone.

20 Claims, 13 Drawing Sheets

(56) References Cited

U.S. PATENT DOCUMENTS

| | | |
|---|---|---|
| 4,388,921 A | 6/1983 | Sutter et al. |
| 4,484,570 A | 11/1984 | Sutter et al. |
| 4,493,317 A | 1/1985 | Klaue |
| 4,641,636 A | 2/1987 | Cotrel |
| 4,692,290 A | 9/1987 | Steele et al. |
| 4,794,918 A | 1/1989 | Wolter |
| 4,828,441 A | 5/1989 | Frasca |
| 4,867,144 A | 9/1989 | Karas et al. |
| 4,946,458 A | 8/1990 | Harms et al. |
| 4,964,403 A | 10/1990 | Karas et al. |
| 5,013,313 A | 5/1991 | Surer |
| 5,041,113 A | 8/1991 | Biedermann et al. |
| 5,053,036 A | 10/1991 | Perren et al. |
| 5,057,111 A | 10/1991 | Park |
| 5,090,854 A | 2/1992 | Hafeli et al. |
| 5,108,399 A | 4/1992 | Eitenmuller et al. |
| 5,127,914 A | 7/1992 | Calderale et al. |
| 5,129,899 A | 7/1992 | Small et al. |
| 5,147,363 A | 9/1992 | Harle |
| 5,151,103 A | 9/1992 | Tepic et al. |
| 5,190,545 A | 3/1993 | Corsi et al. |
| 5,209,751 A | 5/1993 | Farris et al. |
| 5,234,431 A | 8/1993 | Keller |
| 5,269,784 A | 12/1993 | Mast |
| 5,415,658 A | 5/1995 | Kilpela et al. |
| 5,536,268 A | 7/1996 | Griss |
| 5,549,608 A | 8/1996 | Errico et al. |
| 5,554,157 A | 9/1996 | Errico et al. |
| 5,584,834 A | 12/1996 | Errico et al. |
| 5,586,984 A | 12/1996 | Errico et al. |
| 5,607,430 A | 3/1997 | Bailey |
| 5,618,144 A | 4/1997 | Leistner |
| 5,643,261 A | 7/1997 | Schafer et al. |
| 5,647,873 A | 7/1997 | Errico et al. |
| 5,649,927 A | 7/1997 | Kilpela et al. |
| 5,658,285 A | 8/1997 | Marnay et al. |
| 5,665,089 A | 9/1997 | Dall et al. |
| 5,669,911 A | 9/1997 | Errico et al. |
| 5,690,630 A | 11/1997 | Errico et al. |
| 5,702,393 A * | 12/1997 | Pfaifer .......................... 606/328 |
| 5,741,259 A * | 4/1998 | Chan ................................ 606/74 |
| 5,810,823 A | 9/1998 | Klaue et al. |
| 5,810,824 A | 9/1998 | Chan |
| 5,817,094 A | 10/1998 | Errico et al. |
| 5,891,145 A | 4/1999 | Morrison et al. |
| 5,910,142 A | 6/1999 | Tatar |
| 5,935,133 A | 8/1999 | Wagner et al. |
| 5,976,141 A | 11/1999 | Haag et al. |
| 6,010,503 A | 1/2000 | Richelsoph et al. |
| 6,149,653 A | 11/2000 | Deslauriers |
| 6,224,598 B1 | 5/2001 | Jackson |
| 6,241,731 B1 | 6/2001 | Fiz |
| 6,440,136 B1 | 8/2002 | Gambale et al. |
| 6,451,021 B1 | 9/2002 | Ralph et al. |
| 6,454,772 B1 | 9/2002 | Jackson |
| 6,485,491 B1 | 11/2002 | Farris et al. |
| 6,520,965 B2 * | 2/2003 | Chervitz et al. ................ 606/74 |
| 6,524,315 B1 | 2/2003 | Selvitelli et al. |
| 6,540,748 B2 | 4/2003 | Lombardo |
| 6,540,749 B2 | 4/2003 | Schafer et al. |
| 6,554,834 B1 | 4/2003 | Crozet et al. |
| 6,575,975 B2 | 6/2003 | Brace et al. |
| 6,585,739 B2 | 7/2003 | Kuras et al. |
| 6,652,526 B1 | 11/2003 | Arafiles |
| 6,660,004 B2 | 12/2003 | Barker et al. |
| 6,663,635 B2 | 12/2003 | Frigg et al. |
| 6,668,688 B2 | 12/2003 | Zhao et al. |
| 6,669,700 B1 | 12/2003 | Farris et al. |
| 6,682,533 B1 * | 1/2004 | Dinsdale et al. ................ 606/74 |
| 6,689,136 B2 | 2/2004 | Stoffella |
| 6,730,093 B2 | 5/2004 | Saint Martin |
| 6,755,829 B1 | 6/2004 | Bono et al. |
| 6,786,903 B2 | 9/2004 | Lin |
| 6,918,912 B2 | 7/2005 | Seemann |
| 6,960,213 B2 | 11/2005 | Chervitz et al. |
| 6,964,666 B2 | 11/2005 | Jackson |
| 7,001,387 B2 | 2/2006 | Farris et al. |
| 7,018,378 B2 | 3/2006 | Biedermann et al. |
| 7,081,116 B1 | 7/2006 | Carly |
| 7,081,117 B2 | 7/2006 | Bono et al. |
| D536,453 S | 2/2007 | Young et al. |
| 7,204,837 B2 | 4/2007 | Paul |
| 7,250,054 B2 | 7/2007 | Allen et al. |
| 7,252,670 B2 | 8/2007 | Morrison et al. |
| 7,255,699 B2 | 8/2007 | Paul |
| 7,276,070 B2 | 10/2007 | Muckter |
| 7,278,997 B1 | 10/2007 | Mueller et al. |
| 7,320,556 B2 * | 1/2008 | Vagn-Erik .................... 403/385 |
| 7,341,589 B2 | 3/2008 | Weaver et al. |
| 7,407,504 B2 | 8/2008 | Dongar et al. |
| 7,513,905 B2 | 4/2009 | Jackson |
| 7,530,992 B2 | 5/2009 | Biedermann et al. |
| 7,588,575 B2 | 9/2009 | Colleran et al. |
| 7,604,655 B2 | 10/2009 | Warnick |
| 7,618,444 B2 | 11/2009 | Shluzas |
| 7,625,394 B2 | 12/2009 | Molz, IV et al. |
| 7,641,676 B2 | 1/2010 | Mathieu et al. |
| 7,645,294 B2 | 1/2010 | Kalfas et al. |
| 7,655,009 B2 | 2/2010 | Grusin |
| 7,662,172 B2 | 2/2010 | Warnick |
| 7,662,175 B2 | 2/2010 | Jackson |
| 7,666,185 B2 | 2/2010 | Ryan et al. |
| 7,686,834 B2 | 3/2010 | Saint Martin |
| 7,686,835 B2 | 3/2010 | Warnick |
| 7,691,133 B2 | 4/2010 | Partin et al. |
| 7,695,472 B2 | 4/2010 | Young |
| 7,704,271 B2 | 4/2010 | Abdou |
| 7,708,762 B2 | 5/2010 | McCarthy et al. |
| 7,722,651 B2 | 5/2010 | Kwak et al. |
| 7,722,653 B2 | 5/2010 | Young et al. |
| 7,731,735 B2 | 6/2010 | Morrison |
| 7,740,648 B2 | 6/2010 | Young et al. |
| 7,740,649 B2 | 6/2010 | Mosca et al. |
| 7,766,911 B1 | 8/2010 | Navarro et al. |
| 7,766,917 B2 | 8/2010 | Kugler et al. |
| 7,771,458 B2 | 8/2010 | Biedermann et al. |
| 7,780,666 B1 | 8/2010 | Navarro et al. |
| 7,785,327 B1 | 8/2010 | Navarro et al. |
| 7,785,356 B2 | 8/2010 | Biedermann et al. |
| 7,789,900 B2 | 9/2010 | Levy et al. |
| 7,828,826 B2 | 11/2010 | Drewry et al. |
| 7,828,829 B2 | 11/2010 | Ensign |
| 7,833,226 B2 | 11/2010 | Grabowski et al. |
| 7,833,256 B2 | 11/2010 | Biedermann et al. |
| 7,850,717 B2 | 12/2010 | Dewey et al. |
| 7,857,839 B2 | 12/2010 | Duong et al. |
| 7,892,259 B2 | 2/2011 | Biedermann et al. |
| 7,905,883 B2 | 3/2011 | Bruecker et al. |
| 7,905,910 B2 | 3/2011 | Gerlach et al. |
| 7,909,855 B2 | 3/2011 | Drewry et al. |
| 7,909,858 B2 | 3/2011 | Gerlach et al. |
| 7,909,859 B2 | 3/2011 | Mosca et al. |
| 7,909,860 B2 | 3/2011 | Rathbun et al. |
| 7,922,748 B2 | 4/2011 | Hoffman |
| 7,938,829 B2 | 5/2011 | Mullaney |
| 7,942,910 B2 | 5/2011 | Doubler et al. |
| 7,942,911 B2 | 5/2011 | Doubler et al. |
| 7,947,064 B2 | 5/2011 | Bergeron et al. |
| 7,951,172 B2 | 5/2011 | Chao et al. |
| 7,967,849 B2 | 6/2011 | Carson et al. |
| 7,967,851 B2 | 6/2011 | Bickley et al. |
| 7,988,711 B2 | 8/2011 | Erickson et al. |
| 8,002,806 B2 | 8/2011 | Justis |
| 8,012,185 B2 | 9/2011 | Warnick |
| 8,012,186 B2 | 9/2011 | Pham et al. |
| 8,016,866 B2 | 9/2011 | Warnick |
| 8,025,683 B2 | 9/2011 | Morrison |
| 8,048,124 B2 | 11/2011 | Chin et al. |
| 8,048,131 B2 | 11/2011 | Dalton |
| 8,048,132 B2 | 11/2011 | Wu et al. |
| 8,052,724 B2 | 11/2011 | Jackson |
| 8,075,599 B2 | 12/2011 | Johnson et al. |
| 8,080,010 B2 | 12/2011 | Schulz et al. |
| 8,080,040 B2 | 12/2011 | Miller |

(56) References Cited

U.S. PATENT DOCUMENTS

| | | |
|---|---|---|
| 8,083,776 B2 | 12/2011 | Alvarez |
| 8,083,777 B2 | 12/2011 | Butters et al. |
| 8,092,504 B2 | 1/2012 | Warnick |
| 8,105,367 B2 | 1/2012 | Austin et al. |
| 8,114,140 B2 | 2/2012 | Derouet |
| 8,133,262 B2 | 3/2012 | Whipple |
| 8,142,434 B2 | 3/2012 | Bluechel |
| 8,142,481 B2 | 3/2012 | Warnick |
| 8,142,483 B2 | 3/2012 | Drewry et al. |
| 8,147,493 B2 | 4/2012 | Dutoit et al. |
| 8,147,522 B2 | 4/2012 | Warnick |
| 8,167,910 B2 | 5/2012 | Nilsson |
| 8,177,816 B2 | 5/2012 | Schwab |
| 8,177,823 B2 * | 5/2012 | Lake et al. .................. 606/330 |
| 8,192,470 B2 | 6/2012 | Biedermann et al. |
| 8,343,155 B2 | 1/2013 | Fisher et al. |
| 2002/0128654 A1 | 9/2002 | Steger et al. |
| 2003/0187434 A1 | 10/2003 | Lin |
| 2004/0138666 A1 | 7/2004 | Molz et al. |
| 2005/0038428 A1 | 2/2005 | Kelman et al. |
| 2006/0111715 A1 | 5/2006 | Jackson |
| 2006/0195093 A1 | 8/2006 | Jahng |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0235393 A1 | 10/2006 | Bono et al. |
| 2008/0097448 A1 | 4/2008 | Binder et al. |
| 2008/0300599 A1 | 12/2008 | Anapliotis et al. |
| 2009/0204151 A1 | 8/2009 | Bracken |
| 2009/0248077 A1 | 10/2009 | Johns |
| 2009/0287215 A1 | 11/2009 | Fisher et al. |
| 2009/0287255 A1 | 11/2009 | Erickson et al. |
| 2010/0234896 A1 | 9/2010 | Lorenz et al. |
| 2011/0130792 A1 | 6/2011 | Nydegger et al. |

FOREIGN PATENT DOCUMENTS

| | | |
|---|---|---|
| EP | 0791338 A2 | 8/1997 |
| EP | 0600938 B1 | 9/1997 |
| EP | 0791338 B1 | 8/2003 |
| EP | 1075225 B1 | 12/2004 |
| WO | 2004107996 A1 | 12/2004 |

OTHER PUBLICATIONS

Cable Ready Cable Grip System, Comprehensive Cable Grip System, Zimmer, 2001.

Cable-Ready Greater Trochanteric Reattachment, Surgical Technique, Zimmer, 2001, 2008, 2010.

* cited by examiner

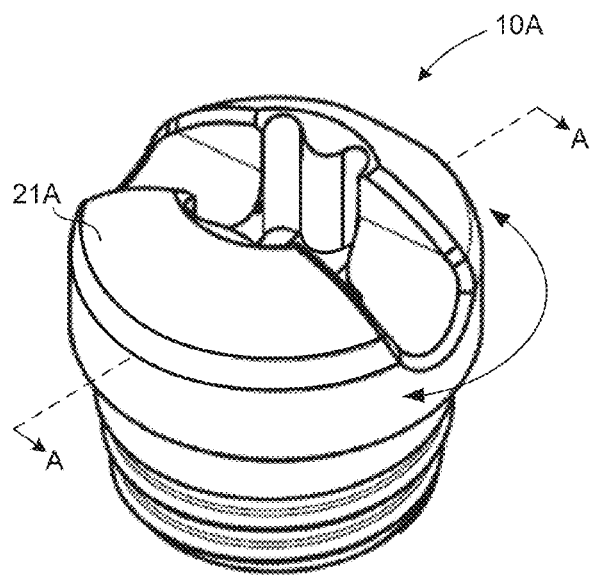
FIG. 7
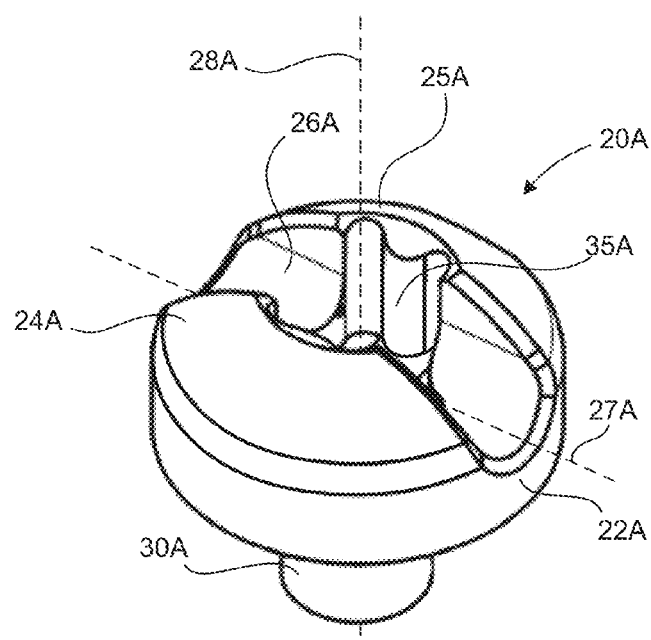
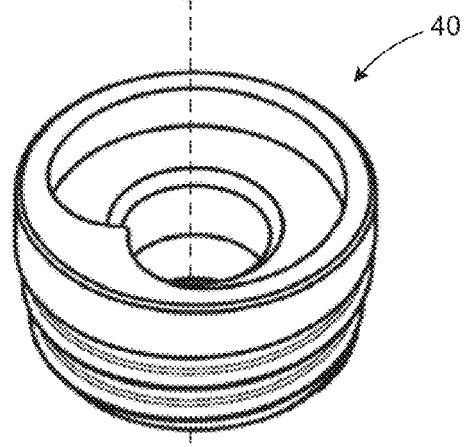
FIG. 6

SECTION A-A

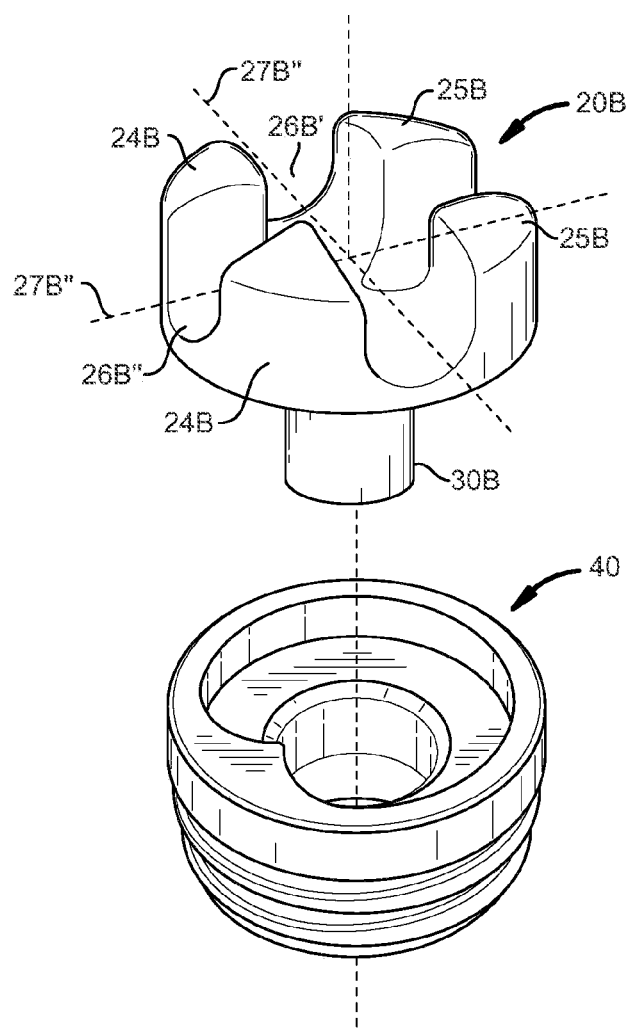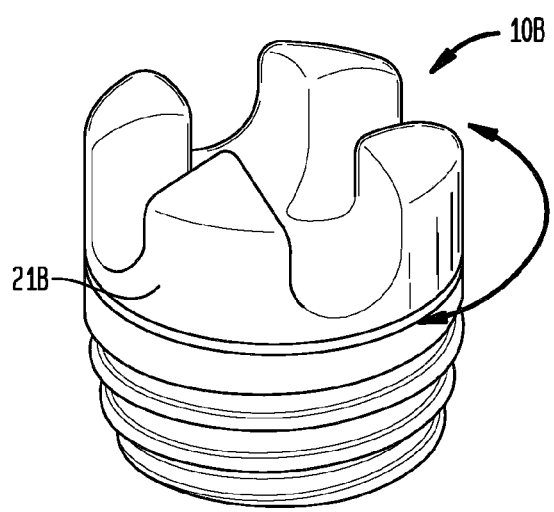

SECTION B-B

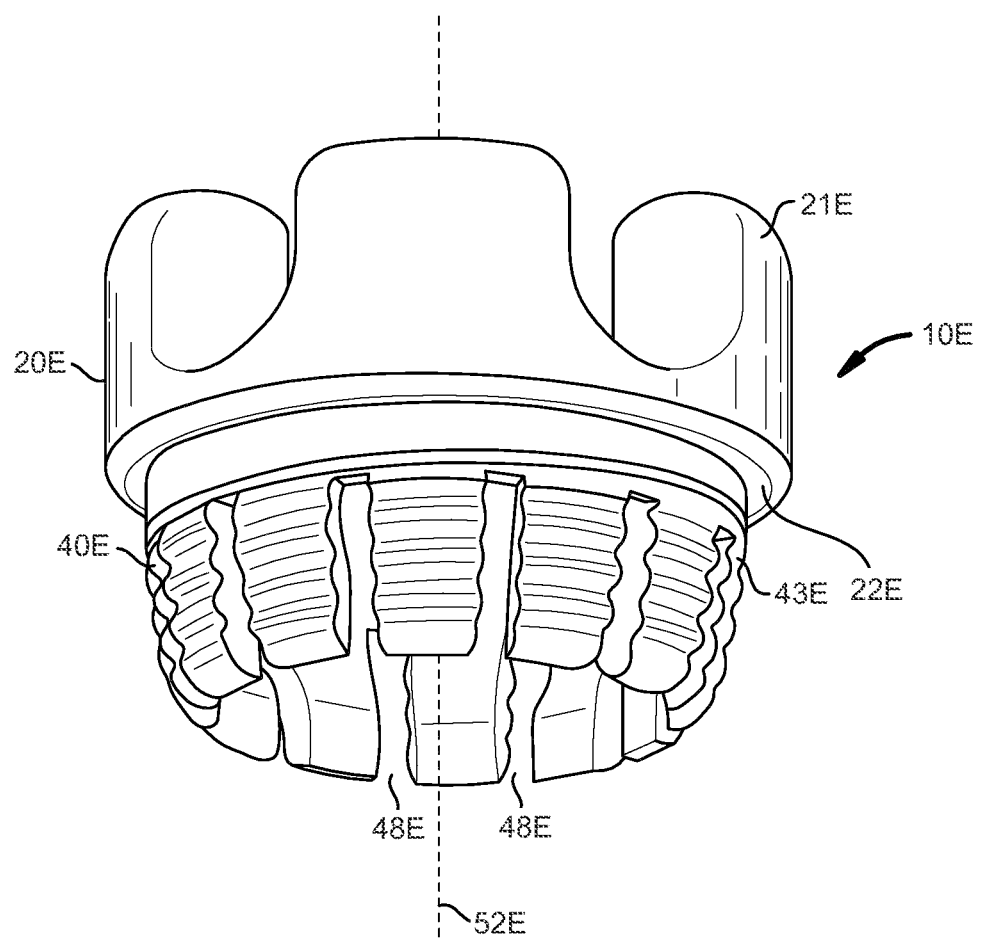

CABLE PLUG

FIELD OF THE INVENTION

The present invention relates to systems for coupling surgical cables to bone plates when reducing bone fractures or repairing fractured bones. More particularly, the invention relates to systems that utilize a cable retaining member, affixed to a bone plate, to receive and retain a surgical cable. In which, the surgical cable may be oriented with respect to the bone at a plurality of angles relative to the longitudinal axis of the bone.

BACKGROUND OF THE INVENTION

Surgical cables are used in many surgical procedures. They are generally used to encircle the bone alone, or the bone and a bone plate, to facilitate fixation of one or more bone fragments. Some bone fixation systems that use surgical cable also use a bone plate having a length sufficient to span the bone fragments, fixation screws to couple the bone plate to the bone, adapters to couple the cable to the bone plate, and crimp devices for securing ends of the cable. In these systems, the surgical cable is generally coupled to the bone or the bone plate at 90° from the longitudinal axis of the bone.

Because the surgical cable is wrapped around the bone and bone plate, as forces act on the cable, the cable may tend to move from its coupled position with respect to the bone plate. As such forces act on the cable, a longitudinal axis of the cable will generally tend to be angled at less than 90° from the longitudinal axis of the bone. This may result in shear stresses and strains in the surgical cable that cause the bone plate to shift relative to the bone.

Some fixation screws function to both couple the bone plate to bone and as a means for coupling the cable at a certain position along a length of the bone plate. If the fixation screws are used to couple the cable to the bone plate, the cable is generally received in a slot or bore in a head portion of the fixation screws. Such fixation screws also act as an adapter. The head portion of the fixation screws are generally integrally coupled to a shaft of the fixation screws but may be a separate component that is coupled to the shaft of the fixation screws.

The adapters and fixation screws explained above generally function to prevent migration of surgical cable along a longitudinal axis of a bone plate. However, these systems do not provide a means of orienting the surgical cable at an angle less than 90° from the longitudinal axis of the bone. Therefore, they cannot sufficiently eliminate the stresses and strains in the surgical cable which may cause shifting of the bone plate.

BRIEF SUMMARY OF THE INVENTION

A first aspect in accordance with one embodiment of the present invention is a cable plug. The cable plug includes a cable retaining member having a head portion, a shaft portion and a stopper member, the head portion having a base surface and at least two receiving members projecting upwardly from the base surface for receiving a surgical cable. The cable plug further includes a fastening member having a top surface, a bottom surface, and an outer circumference, the fastening member having an opening to receive the shaft of the cable retaining member and a boss in the opening. When the cable retaining member is coupled to the fastening member, the cable retaining member is rotatable with respect to the fastening member until the stopper member contacts the boss of the fastening member. When surgical cable is received in the at least two receiving members of the cable retaining member, and the cable plug is assembled to a bone plate, the cable plug provides freedom to rotate the surgical cable without adding torque stresses to the plate and the bone that the plate contacts.

In accordance with one embodiment of this first aspect of the present invention, the at least two receiving members form a channel adapted to receive a surgical cable therein. The surgical cable preferably includes a diameter and the at least two receiving members have oppositely facing surfaces separated by a horizontal distance equal to or greater than the diameter of the surgical cable throughout a vertical length of the at least two receiving members.

In accordance with another embodiment of this first aspect of the present invention, the surgical cable includes a diameter and the at least two receiving members have oppositely facing surfaces separated by a horizontal distance equal to or greater than the diameter of the surgical cable at the base surface of the head portion and less than the diameter of the surgical cable adjacent a top portion of the cable plug.

In accordance with yet another embodiment of this first aspect of the present invention, the cable retaining member includes two sets of at least two receiving members, the two sets of at least two receiving members forming at least two channels adapted to receive surgical cable therein.

In accordance with still yet another embodiment of this first aspect of the present invention, the cable retaining member includes one set of at least two receiving members and a bore hole, the one set of at least two receiving members forming a channel, the bore hole extending through the at least two receiving members, wherein the channel and bore hole are each adapted to receive surgical cable therein. Preferably, the diameter of the channel and bore hole are different such that each are configured to receive a surgical cable with a different diameter.

In accordance with still yet another embodiment of this first aspect of the present invention, the cable retaining member includes an engagement recess that is centrally located between the at least two receiving members, the engagement recess adapted to receive an insertion tool.

In accordance with yet still another embodiment of this first aspect of the present invention, the base surface of the cable retaining member lies adjacent the top surface of the fastening member when the cable retaining member is coupled to the fastening member.

In accordance with yet still another embodiment of this first aspect of the present invention, the opening in the fastening member is irregularly shaped and includes a top portion adapted to receive the stopper member and a bottom portion adapted to receive the shaft of the cable retaining member when the cable retaining member is coupled to the fastening member. The top portion of the opening extends at least 90° about a longitudinal axis of the cable plug. Preferably, the top portion of the opening extends 270° about a longitudinal axis of the cable plug.

In accordance with yet still another embodiment of this first aspect of the present invention, the opening in the fastening member is irregularly shaped and includes a top portion shaped as a keyhole and adapted to receive the shaft and stopper member of the cable retaining member therethrough and a bottom portion adapted to house the stopper member when the cable retaining member is being rotated with respect to the fastening member.

A second aspect in accordance with one embodiment of the present invention is a cable plug. The cable plug includes a cable retaining member having a head portion and a shaft portion, the head portion having a base surface and at least two receiving members projecting upwardly from the base surface, the shaft portion extending downwardly from the base surface. The cable plug further includes a fastening member having a top surface, a bottom surface, and an outer circumference, the fastening member having an opening in the top surface adapted to receive the shaft of the cable retaining member. The cable plug further includes a stopper member engaged to the cable retaining member, wherein when the cable retaining member is coupled to the fastening member, the cable retaining member may be rotated with respect to the fastening member in a first rotational direction about a longitudinal axis of the cable plug until the stopper member contacts a first stop surface of the fastening member.

According to one embodiment of this second aspect, when the cable retaining member is operatively coupled to the fastening member, the cable retaining member may be rotated with respect to the fastening member in a second rotational direction opposite the first rotational direction about a longitudinal axis of the cable plug until the stopper contacts a second stop surface of the fastening member.

A third aspect in accordance with one embodiment of the present invention is a method for securing a bone plate to a bone of a patient. The method includes inserting a cable plug into a hole in the bone plate, contacting the bone with the bone plate, and wrapping surgical cable having a longitudinal axis around the bone and the bone plate. The method further includes rotating a cable retaining member of the cable plug about a longitudinal axis of the cable plug until a longitudinal axis of a channel formed by at least two receiving members of the cable retaining member are parallel to the longitudinal axis of the surgical cable, placing the surgical cable in the channel of the cable retaining member, tightening the surgical cable until the bone plate is secured to the bone, and crimping first and second ends of the surgical cable.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 6 is an exploded perspective view of another embodiment of a cable retaining member of the present invention and the fastening member shown in FIGS. 3A-B.

FIG. 7 is an assembled perspective view of the cable retaining member and fastening member shown in FIG. 6.

FIG. 9 is an exploded perspective view of another embodiment of a cable retaining member of the present invention and the fastening member shown in FIGS. 3A-B.

FIG. 10 is an assembled perspective view of the cable retaining member and fastening member shown in FIG. 9.

FIG. 18 is a perspective view of one embodiment of a cable plug of the present invention having a cable retaining portion shown in FIGS. 7-8 integrated with an embodiment of a fastening portion adapted for direct insertion into an aperture of a bone plate.

DETAILED DESCRIPTION OF SPECIFIC EMBODIMENTS

Figure 1A:
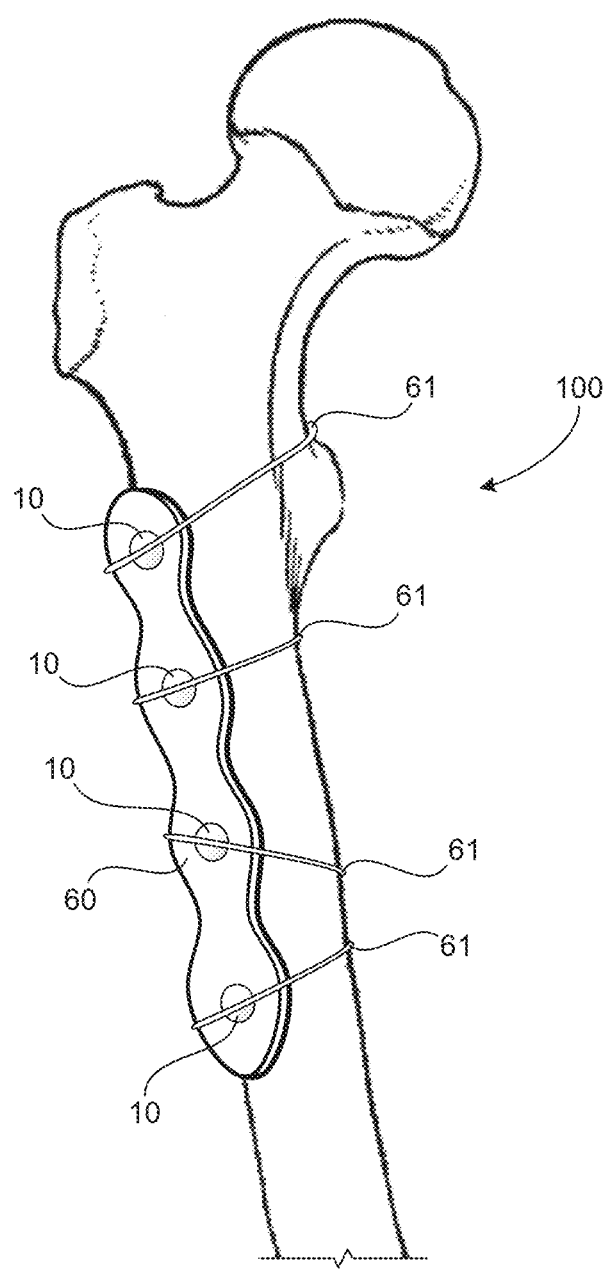
FIG. 1A is a perspective view of one embodiment of a fixation system of the present invention showing a cable plug coupling a surgical cable to a bone plate.

Referring to FIG. 1A, there is shown a bone fixation system 100 engaged to a portion of a femur bone 12. Bone fixation system 100 includes a surgical cable 61 coupled to a bone plate 60 via a cable plug 10. As shown in FIG. 1A, a surgical cable 61 is wrapped around femur bone 12 just above the lesser trochanter, another surgical cable 61 is wrapped around the femoral shaft just below the lower trochanter, and two more surgical cables 61 are wrapped about the femoral shaft some distance below the lesser trochanter. In each instance, surgical cable 61 may be received and retained by cable plug 10 at a plurality of angles relative to longitudinal axis of the bone.

Figure 1B:
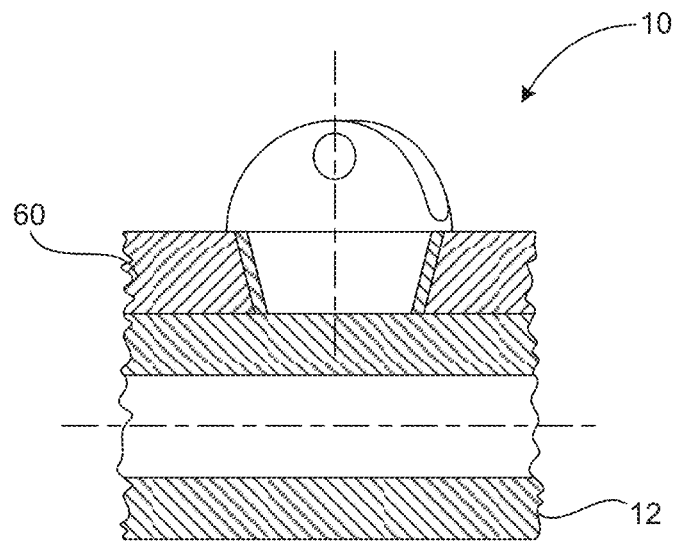
FIG. 1B is a partial cross-section view of a portion of the fixation system shown in FIG. 1A.
Figure 1C:
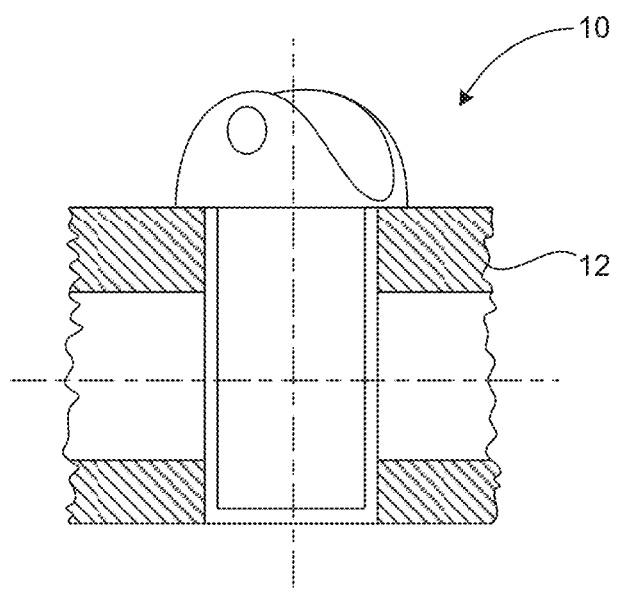
FIG. 1C is a partial cross-section view of one embodiment of a cable plug coupled directly to a bone of a patient.

FIG. 1B is a partial cross-section view of a portion of fixation system 100 shown in FIG. 1A showing cable plug 10 located in an aperture of bone plate 60 with bone plate 60 lying adjacent to a portion of femur bone 12. In reference to FIG. 1C, another embodiment of a cable plug 10 is shown coupled directly to a portion of a bone of a patient without a bone plate lying adjacent to the bone.

Figure 2A:
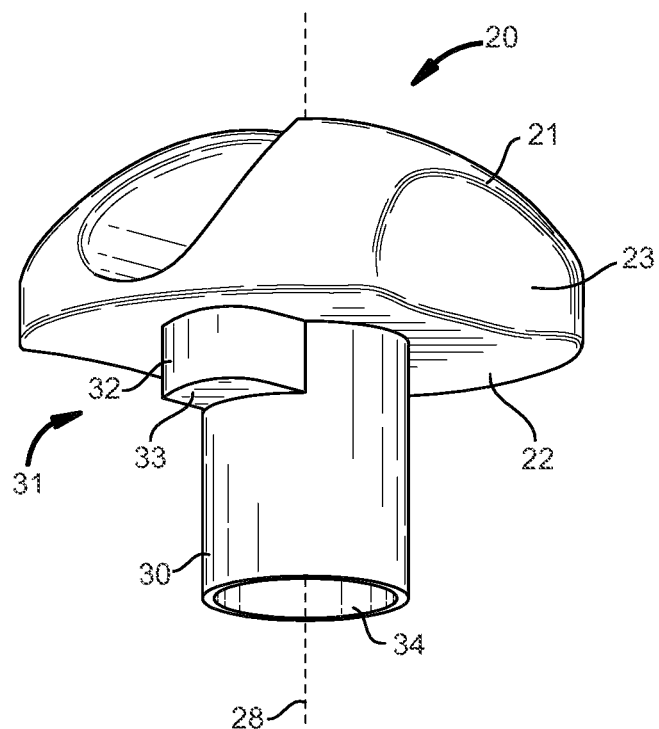
FIG. 2A is a perspective view of one embodiment of a cable retaining member of the present invention.
Figure 2B:
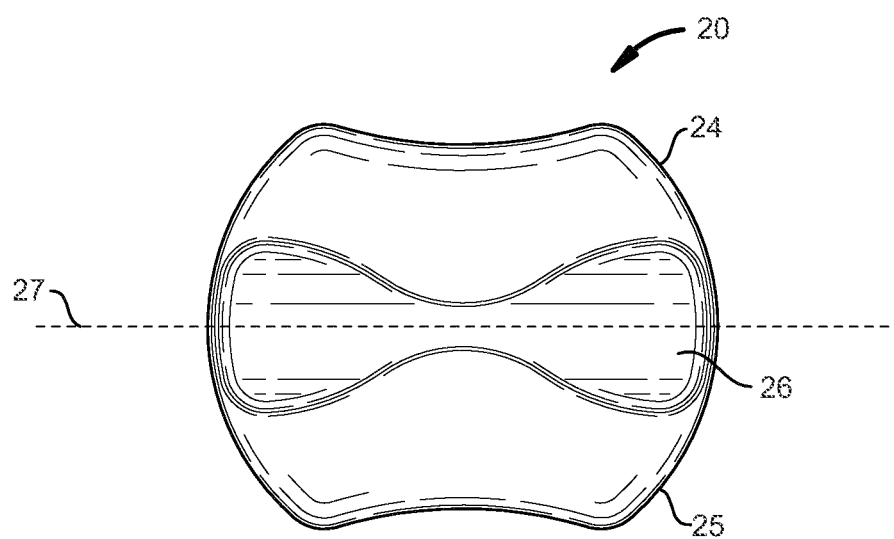
FIG. 2B is a top view of the cable retaining member shown in FIG. 2A.
Figure 3A:
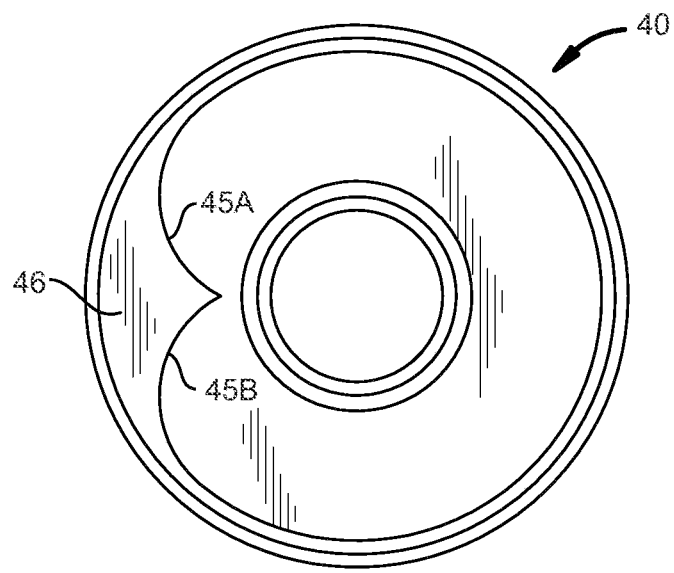
FIG. 3A is a top view of one embodiment of a fastening member of the present invention.
Figure 3B:
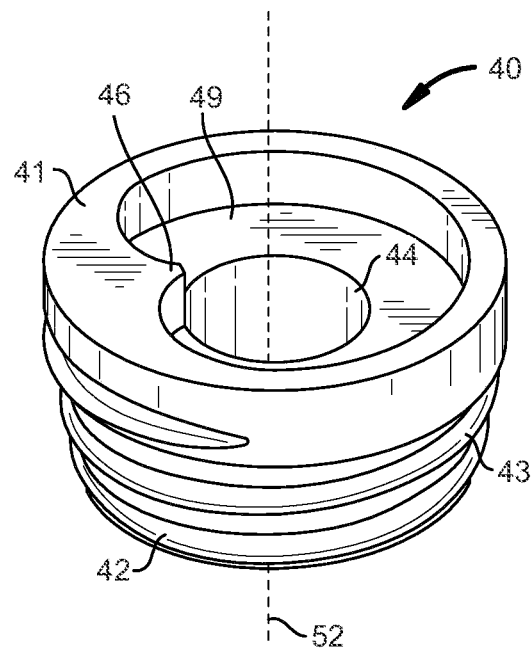
FIG. 3B is a perspective view of the fastening member shown in FIG. 3A.

In a preferred embodiment, cable plug 10 comprises a cable retaining member 20 as shown for example in FIGS. 2A-2B and a fastening member 40 as shown for example in FIGS. 3A-3B. Referring to FIGS. 2A-2B, cable retaining member 20 includes a head portion 21, a base surface 22, and a shaft portion 30 extending downwardly from base surface 22. Head portion 21 of cable retaining member 20 includes a cable receiving structure such as a channel or a bore hole. In a preferred embodiment, the cable receiving structure is comprised of two cable receiving members 24, 25 projecting upwardly from base surface 22. However, the cable receiving structure described herein may also be formed by a single cable receiving member, or by a plurality of such members. Cable receiving members 24, 25 each have an outer face 23.

Outer faces 23 are preferably concave and are adapted to be grasped by fingers of a user such that the head portion can easily be manipulated by hand.

As shown in FIGS. 2A-2B, cable receiving members 24, 25 are preferably separated by a distance equal to or greater than the diameter of surgical cable 61 proximate base surface 22, yet separated by a distance less than the diameter of surgical cable 61 proximate the top of head portion 21. In this configuration, the at least two cable receiving members 24, 25 form an upward facing channel 26 with a longitudinal axis 27 that is perpendicular to a longitudinal axis 28 of shaft portion 30. Surgical cable 61 may then be placed by force, or by use of an insertion tool, into channel 26, as may be further adapted to retain surgical cable 61 therein.

In this preferred embodiment, as shown particularly in FIG. 2A, a stopper member 31 is integral with cable retaining member 20. Stopper member 31 projects downwardly from base surface 22, outwardly from shaft portion 30 of cable retaining member 20, and preferably includes a curved outer surface 32 and a flat bottom surface 33. The distal end of shaft 30 preferably includes a spherically shaped recess portion or bore hole 34 adapted to receive a blocking member (not shown). As described fully with reference to FIG. 8 below, the blocking member may be inserted into bore hole 34 as a means to secure cable retaining member 20 to fastening member 40.

Referring to FIGS. 3A-3B, a preferred embodiment of fastening member 40 includes a top surface 41, a bottom surface 42, an outer circumference 43, and an opening 44 having a longitudinal axis 52. The opening 44 preferably extends through top surface 41 and bottom surface 42 thereof. Opening 44 may be irregularly shaped, including a top portion 49 and a bottom portion 51. In the preferred embodiment, top surface 41 has a boss 46 adapted to receive stopper member 31, and a bottom portion 51 adapted to receive shaft 30 of cable retaining member 20. In this embodiment, top portion 49 of opening 44 preferably terminates in a radial direction about longitudinal axis 52 at first stop surface 45A and second stop surface 45B of boss 46, as shown particularly in FIG. 3A. Top portion 49 of opening 44 extends at least 90° and preferably approximately 270° about longitudinal axis 52.

Figure 4:
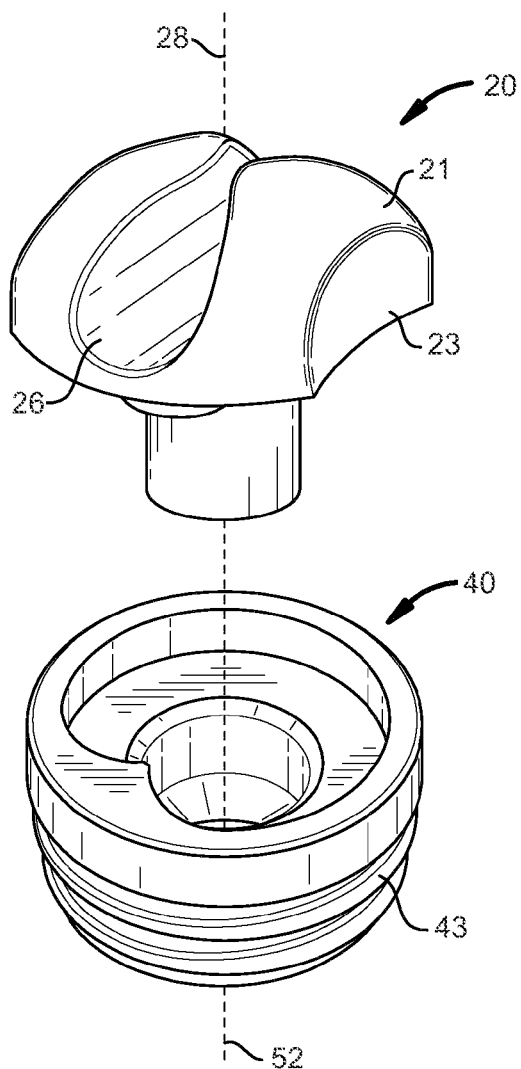
FIG. 4 is an exploded perspective view of the cable retaining member of FIGS. 2A-B and the fastening member of FIGS. 3A-B.
Figure 5:
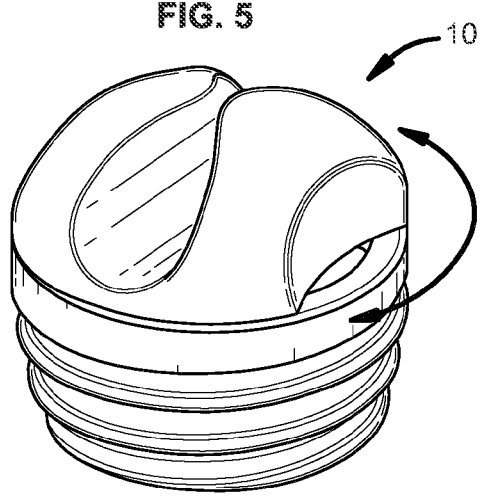
FIG. 5 is an assembled perspective view of the cable retaining member and fastening member shown in FIG. 4.

Referring to the preferred embodiment shown in FIGS. 4-5, cable retaining member 20 may be coupled to fastening member 40 to form cable plug 10 prior to insertion into a bone plate, such as bone plate 60. When coupled, cable plug 10 is preferably affixed to bone plate 60 using outer circumference 43 configured with straight or tapered threads. This configuration permits rotation of cable retaining member 20 with respect to fastening member 40, in a first or second rotational direction, about longitudinal axes 28 and 52. In accordance with this invention, surgical cable 61 may therefore be retained within channel 26 of head portion 21 and oriented at a plurality of angles relative to the bone.

In an alternate embodiment, cable retaining member 20 may also include a plurality of protrusions or recesses located around a circumference thereof, the plurality of protrusions or recesses adapted to couple to a plurality of corresponding protrusions or recesses around a circumference of fastener member 40. This configuration permits orientation of cable retaining member 20 with respect to fastening member 40 about longitudinal axes 28 and 52. Similar to above, surgical cable 61 may therefore be retained within channel 26 of head portion 21 and oriented at a plurality of angles relative to the bone.

Alternatively, as shown in FIGS. 6-7, cable receiving members 24A, 25A may also be separated by a distance equal or greater than the diameter of surgical cable 61 proximate base surface 22A, and remain separated by said distance proximate the top of head portion 21A. Here also, the at least two cable receiving members 24A, 25A form an upward facing channel 26A with a longitudinal axis 27A that is perpendicular to a longitudinal axis 28A of shaft portion 30A. In this embodiment, channel 26A may be further adapted to receive an insertion tool by inclusion of an engagement recess 35A in a hexagonal star shape as shown, or in any other suitable shape.

Figure 8:
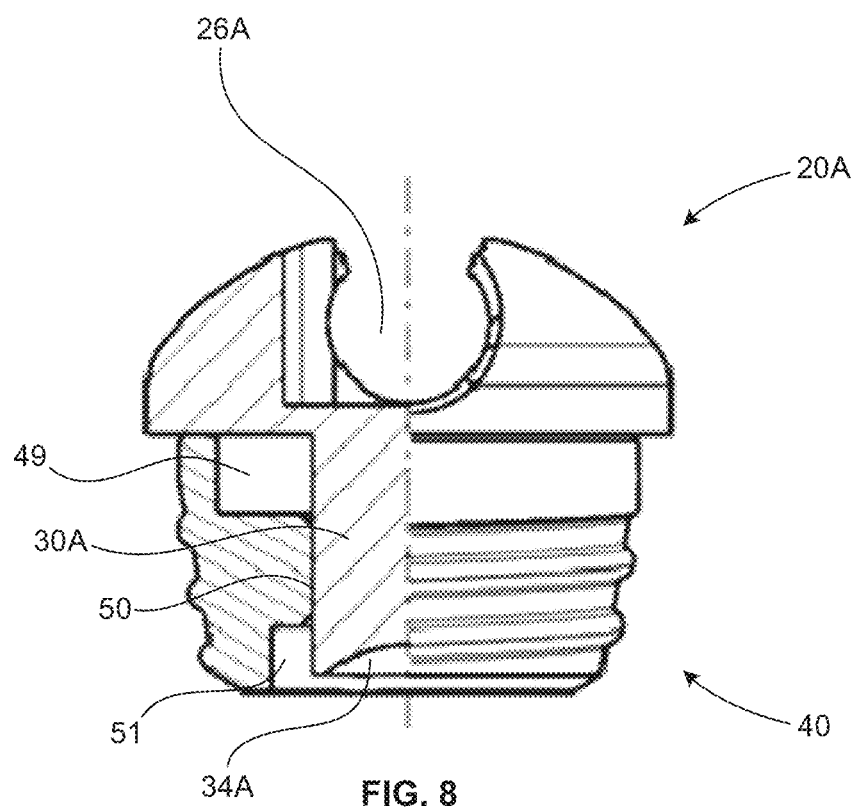
FIG. 8 is a partial cross-sectional view of the assembled cable retaining member and fastening member shown in FIG. 7 taken along line A-A.

As shown in FIG. 8, the distal end of shaft 30A preferably includes a bore hole 34A adapted to receive a blocking member (not shown) once shaft 30A has been passed through opening 44 of fastening member 40. Opening 44 is preferably irregularly shaped and includes a top portion 49 an intermediate portion 50, and a bottom portion 51. The blocking member may, for example, be comprised of an integral hemisphere of deformable material that is pushed back into bore hole 34A. Alternatively, the blocking member may be an external ball bearing of a diameter slightly larger than that of bore hole 34. To couple cable receiving member 20C and fastening member 40, the blocking member is forcefully inserted into bore hole 34 after shaft 30A has passed through opening 44 to increase the diameter of the distal end of shaft portion 30A beyond the diameter of intermediate portion 50. The resulting interference fit effectively secures cable retaining member 20A to fastening member 40 during insertion of cable plug 10 into bone plate 60.

An alternate embodiment is shown in FIGS. 9-10, in which head portion 21B of cable retaining member 20B includes two sets of at least two cable receiving members, 24B, 25B. Each of the two sets of at least two cable receiving members may remain separated by a distance equal or greater to the diameter of surgical cable 61 throughout their respective vertical lengths. In this configuration, cable receiving members 24B, 25B form at least two upward facing channels, 26B', 26B", with a pair of corresponding longitudinal axes, 27B', 27B" that are both perpendicular to a longitudinal axis 28B of shaft portion 30B. In accordance with this embodiment of the invention, surgical cable 61 may therefore be retained within both channel 26B' and 26B" of head portion 21B and oriented a plurality of angles relative to the bone.

Figure 11:
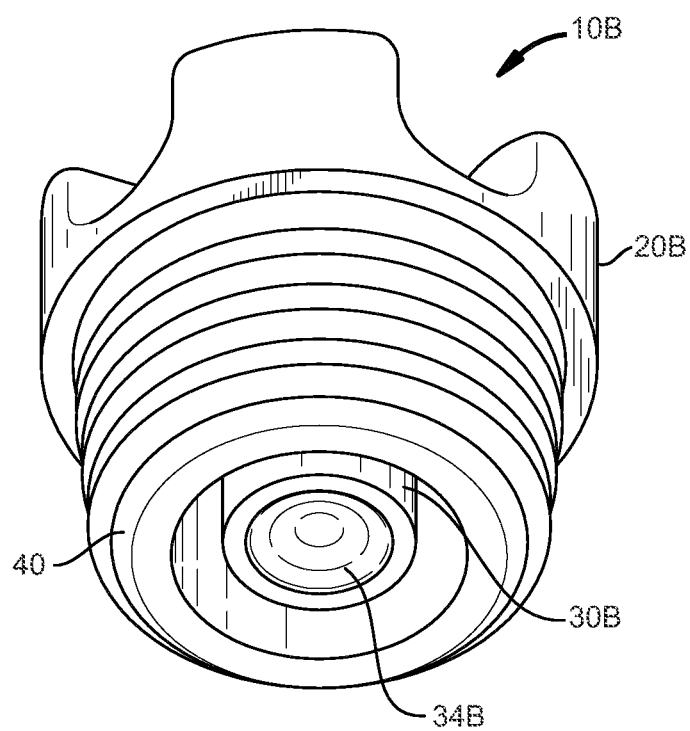
FIG. 11 is a bottom view of the assembled cable retaining member and fastening member shown in FIG. 10.

As shown in FIG. 11, the distal end of shaft 30B may also include a bore hole 34B adapted to receive a blocking member (not shown). Similar to the above description regarding FIG. 8, the blocking member may be inserted into bore hole 34B as a means to secure cable retaining member 20 to fastening member 40.

Figure 13:
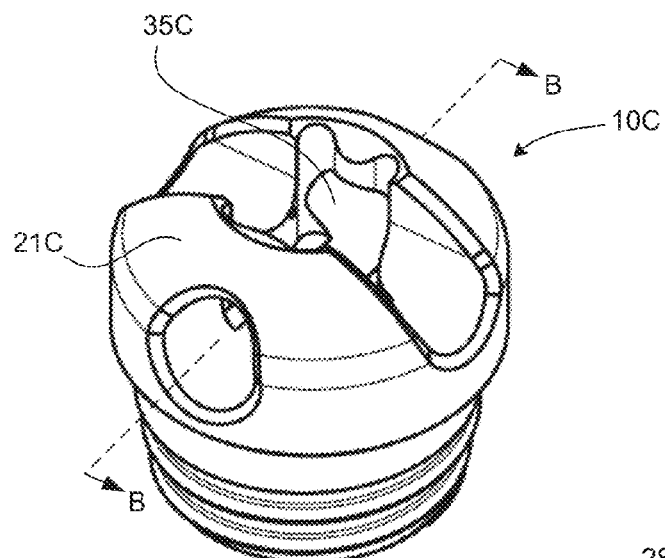
FIG. 13 is an assembled perspective view of the cable retaining member and fastening member shown in FIG. 12.
Figure 12:
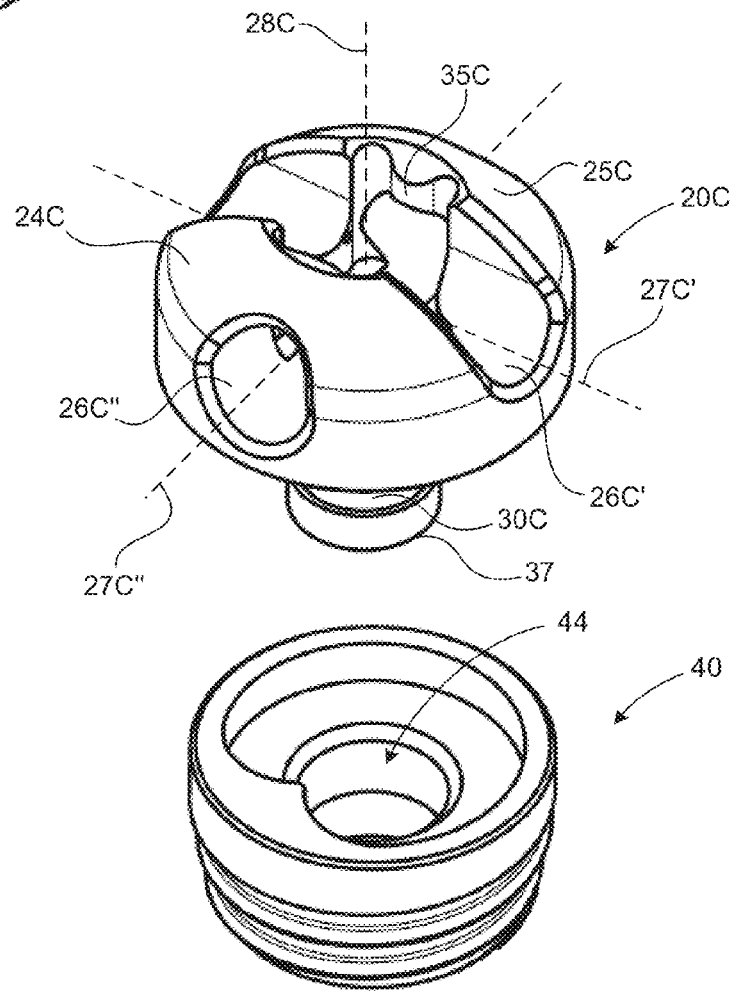
FIG. 12 is an exploded perspective view of another embodiment of a cable retaining member of the present invention and the fastening member shown in FIGS. 3A-B.

FIGS. 12-13 depict yet another embodiment of a cable plug, such as cable plug 10C. In this embodiment, cable receiving members 24C, 25C form an upward facing channel 26C', having a longitudinal axis 27C', adapted to intersect with a channel bore 26C", having a longitudinal axis 27C". According to this embodiment, cable receiving members 24C, 25C, form channel 26C' and bore hole 26C", both perpendicular to a longitudinal axis 28C of shaft portion 30C. Surgical cable 61 may then be threaded into bore hole 26C" and further placed by force, or by use of an insertion tool, into channel 26C', either of which may be further adapted to retain surgical cable 61 therein. As shown, the intersection of channel 26C' and bore hole 26C" may be further adapted to engage an insertion tool by inclusion of recess 35C in a hexagonal star shape as shown, or in any other suitable shape.

Figure 14:
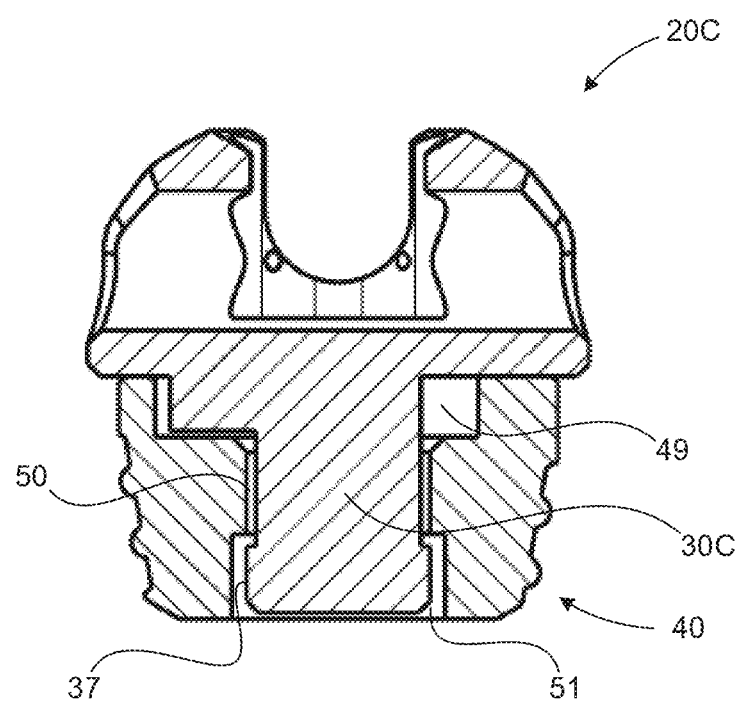
FIG. 14 is a cross-sectional view of the assembled cable retaining member and fastening member shown in FIG. 13 taken along line B-B.

As shown in FIG. 14, the distal end of shaft 30C may also include a band 37, both of which are configured to be received in opening 44 of fastening member 40. Opening 44 of fastening member 40 is preferably irregularly shaped and includes a top portion 49 an intermediate portion 50, and a bottom portion 51. Intermediate portion 50 has a diameter at least slightly less than the diameter of band 37, and band 37 is preferably made of a deformable material. To couple cable receiving member 20C and fastening member 40, downward pressure is applied to cable receiving member 20C until band 37 is fully located in bottom portion 53C of opening 44. Pressing shaft portion 30C with band 37 into opening 44 establishes an interference fit between cable receiving member 20C and fastening member 40, thus ensuring that cable retaining member 20C is secured to fastening member 40 during insertion of cable plug 10C into bone plate 60.

Figure 15:
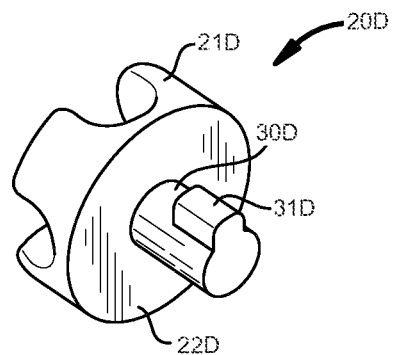
FIG. 15 is a perspective view of another embodiment of a cable retaining member of the present invention.
Figure 16:
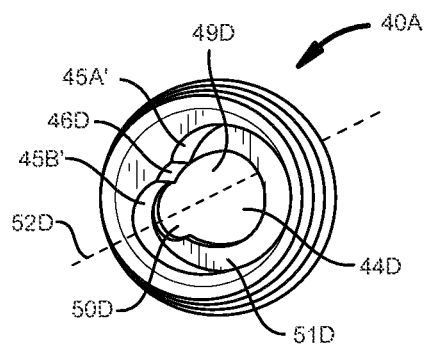
FIG. 16 is a perspective view of another embodiment of a fastening member of the present invention.
Figure 17:
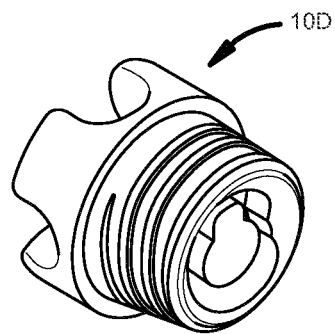
FIG. 17 is an assembled perspective view of the cable retaining member shown in FIG. 15 and fastening member shown in FIG. 16.

Referring to FIGS. 15-17, a stopper member 31D is preferably engaged to a distal end of shaft portion 30D, thus forming an "L" shape with respect to base surface 22D. In this configuration, both top portion 49D and bottom portion 51D of opening 44D are adapted to receive both shaft portion 30D and stopper member 31D through a keyhole 50D. Bottom portion 51D of opening 44D terminates in a radial direction about longitudinal axis 52D at first stop surface 45A' and second stop surface 45B' of boss 46D. Similar to above, bottom portion 51D of opening 44D extends at least 90° and preferably approximately 270° about longitudinal axis 52D, as shown particularly in FIG. 16.

In yet another embodiment, cable plug 10 comprises a variation of cable retaining members 20, 20A, 20B, 20C, or 20D, as shown for example in FIG. 4, 6, 9, 12 or 15, adapted for direct insertion into bone plate 60. All the features of opening 44, 44D with top portion 49, 49D and bottom portion 51, 51D, are milled, or otherwise formed, into bone plate 60 so as to permit cable retaining members 20, 20A, 20B, 20C, or 20D to be coupled directly with bone plate 60. In accordance with this embodiment, surgical cable 61 can thus be retained within head portions 21, 21A, 21B, 21C, or 21D of cable retaining member 20, 20A, 20B, 20C, or 20D at a plurality of angles relative to the bone.

Alternatively still, as shown in FIG. 18, cable plug 10E may comprise a cable retaining portion 20E integrated with a fastening portion 40E in a monoblock assembly. This embodiment may include any variation of the cable retaining member discussed above. Outer circumference 43E is preferably threaded and broken by one or more slots 48E. The monoblock assembly of cable retaining portion 20E and fastening portion 40E is pressed into bone plate 60 until base surface 22E lies adjacent to the top of bone plate 60. Similar to above, this configuration permits rotation of cable retaining portion 20E, with respect to bone plate 60, in a first or second rotational direction, about longitudinal axis 52E. In accordance with this embodiment, surgical cable 61 may therefore be retained within head portion 21E of cable retaining portion 20E and oriented a plurality of angles relative to the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described by the appended claims.

The invention claimed is:

1. A cable plug comprising:
    a cable retaining member having a head portion, a shaft portion and a stopper member, the head portion having a base surface and a receiving member projecting upwardly from the base surface for receiving a surgical cable therein; and
    a fastening member having a first portion, a second portion, and a longitudinal axis, the first portion being adapted to receive the shaft of the cable retaining member, the second portion having an interior sidewall that defines an opening and a boss extending outwardly from the interior sidewall towards the longitudinal axis,
    wherein the stopper member is proximate to the boss when the shaft of the cable retaining member is received within the opening of the fastening member so that the cable retaining member is freely rotatable with respect to the fastening member until the stopper member contacts the boss.

2. The cable plug of claim 1, wherein there are at least two receiving members that form a channel adapted to receive a surgical cable therein.

3. The cable plug of claim 2, wherein the surgical cable includes a diameter and a width of the channel is equal to or greater than the diameter of the surgical cable.

4. The cable plug of claim 3, wherein each of the at least two cable receiving members has an exterior surface that defines a bore hole extending through each of the at least two receiving members, and wherein the channel and each bore hole are each adapted to receive a surgical cable therein.

5. The cable plug of claim 3, wherein the width of the channel is equal to or greater than the diameter of the surgical cable at the base surface of the head portion and less than the diameter of the surgical cable adjacent a top portion of the cable plug.

6. The cable plug of claim 1, wherein there are two sets of at least two receiving members, the two sets of at least two receiving members forming at least two channels adapted to receive surgical cable therein.

7. The cable plug of claim 1, wherein an engagement recess is centrally located on the head portion, the engagement recess adapted to receive an insertion tool.

8. The cable plug of claim 1, wherein the stopper member is integral with the shaft of the cable retaining member.

9. The cable plug of claim 8, wherein the stopper member is also integral with the cable retaining member adjacent an intersection of the base surface and the shaft portion thereof.

10. The cable plug of claim 1, wherein a bottom surface of the head portion of the cable retaining member lies adjacent a top surface of the fastening member when the shaft of the cable retaining member is received within the opening of the fastening member.

11. The cable plug of claim 1, wherein a securing means is insertable into a hollow portion of the shaft of the cable retaining member for preventing the uncoupling of the cable retaining and fastening members.

12. The cable plug of claim 1, wherein the boss has a first stop surface and a second stop surface, and wherein the cable retaining member is freely rotatable with respect to the fastening member in a first rotational direction until the stopper member engages the first stop surface and in a second rotational direction until the stopper member engages the second stop surface.

13. A cable plug comprising:
    a cable retaining member having a head portion, a shaft portion, and a stopper member, the head portion having a base surface and a receiving member projecting upwardly from the base surface for receiving a surgical cable therein; and
    a fastening member having a top portion, a bottom portion, and a longitudinal axis, the top portion having an interior sidewall that defines an irregular shaped opening and a boss extending outwardly from the interior sidewall towards the longitudinal axis,
    wherein the boss is proximate to the stopper member when the shaft and the stopper member of the cable retaining member are received in the bottom portion of the fastening member so that the cable retaining member is freely rotatable with respect to the fastening member until the stopper member contacts the boss.

14. The cable plug of claim 13, wherein the irregularly shaped opening of the top portion of the fastening member has a cross section having a circular portion that extends approximately 270° about the longitudinal axis of the fastening member.

15. The cable plug of claim 13, wherein the irregularly shaped opening in the top portion of the fastening member has a keyhole shaped cross-section adapted to receive the shaft portion and the stopper member of the cable retaining member therethrough, and wherein the bottom portion of the fastening member is adapted to house the stopper member when the cable retaining member is being rotated with respect to the fastening member.

16. The cable plug of claim 13, wherein the fastening member has an threaded exterior surface.

17. The cable plug of claim 13, wherein a securing means is insertable into a hollow portion of the shaft of the cable retaining member for preventing the uncoupling of the cable retaining member and the fastening member.

18. A cable plug comprising:
a cable retaining member having an integral stopper member, a head portion having a base surface, at least two receiving members projecting upwardly from the base surface, and a shaft portion extending downwardly from the base surface; and
a fastening member having a top portion, a bottom portion, and a longitudinal axis, the top portion having an internal sidewall that defines an irregularly shaped opening with a boss extending outwardly from the internal sidewall towards the longitudinal axis, the bottom portion being adapted to receive the shaft portion of the cable retaining member,
wherein receipt of the shaft portion of the cable retaining member in the bottom portion of the fastening member operatively couples the fastening member to the cable retaining member, and
wherein when the cable retaining member is operatively coupled to the fastening member, the cable retaining member may be rotated with respect to the fastening member in a first rotational direction about the longitudinal axis of the fastening member until the integral stopper member contacts a first stop surface of the boss.

19. The cable plug of claim 18, wherein when the cable retaining member is operatively coupled to the fastening member, the cable retaining member may be rotated with respect to the fastening member in a second rotational direction opposite the first rotational direction about the longitudinal axis of the fastening member until the stopper contacts a second stop surface of the boss.

20. A method for securing a bone plate to a bone of a patient, the method comprising of:
inserting a cable plug into a hole in the bone plate;
contacting the bone with the bone plate;
wrapping surgical cable having a longitudinal axis around the bone and the bone plate;
rotating a cable retaining member of the cable plug about a longitudinal axis of the cable plug until a longitudinal axis of a channel formed by at least two receiving members of the cable retaining member is parallel to at least a portion of the longitudinal axis of the surgical cable;
placing the surgical cable in the channel of the cable retaining member;
tightening the surgical cable until the bone plate is secured to the bone; and
crimping first and second ends of the surgical cable to secure the bone plate to the bone of the patient.

\* \* \* \* \*